US008008336B2

(12) United States Patent
Ie et al.

(10) Patent No.: US 8,008,336 B2
(45) Date of Patent: Aug. 30, 2011

(54) CONDENSATION COMPOUND BETWEEN FLUORINATED CYCLOPENTANE RING AND AROMATIC RING, AND PROCESS FOR PRODUCING THE SAME

(75) Inventors: Yutaka Ie, Osaka (JP); Yoshio Aso, Osaka (JP)

(73) Assignee: Sumitomo Chemical Co., Ltd., Tokyo (JP)

( * ) Notice: Subject to any disclaimer, the term of this patent is extended or adjusted under 35 U.S.C. 154(b) by 798 days.

(21) Appl. No.: 11/885,913

(22) PCT Filed: Mar. 2, 2006

(86) PCT No.: PCT/JP2006/303998
§ 371 (c)(1),
(2), (4) Date: Mar. 17, 2008

(87) PCT Pub. No.: WO2006/095634
PCT Pub. Date: Sep. 14, 2006

(65) Prior Publication Data
US 2008/0207922 A1    Aug. 28, 2008

(30) Foreign Application Priority Data
Mar. 9, 2005    (JP) .................... 2005-065946

(51) Int. Cl.
*A61K 31/409* (2006.01)
*C07D 495/22* (2006.01)
(52) U.S. Cl. ...................................... 514/410; 548/421
(58) Field of Classification Search .................. 514/412, 514/410; 548/515, 421
See application file for complete search history.

(56) References Cited

U.S. PATENT DOCUMENTS

| 2003/0003379 | A1 | 1/2003 | Lee et al. |
| 2004/0119049 | A1 | 6/2004 | Heeney et al. |
| 2004/0183068 | A1 | 9/2004 | Ong et al. |
| 2004/0186266 | A1 | 9/2004 | Jiang et al. |
| 2004/0230021 | A1 | 11/2004 | Giles et al. |
| 2005/0106804 | A1 | 5/2005 | Aviram |

FOREIGN PATENT DOCUMENTS

| DE | 281 187 | 8/1990 |
| EP | 1 279 689 | 1/2003 |
| JP | 6-135869 | 5/1994 |
| JP | 03-050811 | 3/1997 |
| JP | 2001-354600 | 12/2001 |
| JP | 2004-186695 | 7/2004 |
| JP | 2004-288859 | 10/2004 |
| JP | 2004-339516 | 12/2004 |
| WO | 03/010778 | 2/2003 |
| WO | 2004/018560 | 3/2004 |

OTHER PUBLICATIONS

Khanh, et al., "First Synthesis of Isothianinhydrin, the Second Thiophene Isostere of Ninhydrin", Synlett 1999, No. 9, 1450-1452.
Izumi, et al., "Synthesis and Spectroscopic Properties of a Series of β-Blocked Long Oligothiophenes up to the 96-mer: Revaluation of Effective Conjugation Length", J. Am. Chem. Soc. 2003, 125, 5286-5287.
Cousseau, et al. "Tetrabutylammonium and polymer-supported dihydrogentrifluoride: new reagents for the hydrofluorination of activated acetylenic bonds", Bulletin de la Société Chimique de France 1986 No. 6, 910-915.
Yokoyama, et al., "Improved O/S Exchange Reagents", Synthesis, Oct. 1984, 827-829.
Cava, et al., "Thionation Reactions of Lawesson's Reagents", Tetrahedron Report No. 192, Tetrahedron vol. 41, No. 22, pp. 5061-5087, 1985.
Yoshifuji, et al., "2,4-Di-*t*-butyl-6-methoxyphenyldithioxophosphorane as a Probe for Mechanistic Studies of Lawesson's Reagent", Tetrahedron Letters, 1994, vol. 35, No. 25, pp. 4379-4382.

(Continued)

*Primary Examiner* — Taofiq A Solola
(74) *Attorney, Agent, or Firm* — Hamre, Schumann, Mueller & Larson, P.C.

(57) ABSTRACT

A condensation compound of a fluorinated cyclopentane ring and an aromatic ring, which is useful, for example, for electronic materials, and a process for producing the same are provided. For instance, according to Scheme 1 below, a compound (68) containing a condensed structure formed of a hexafluorocyclopentane ring and an aromatic ring is synthesized. The aromatic ring is not limited to a thiophene ring but can be any ring and any substituent can be used. Thus a compound containing a condensed ring structure formed of a hexafluorocyclopentane ring and an aromatic ring, particularly, for instance, a thiophene ring, which was impossible to produce conventionally, can be produced easily with high yield. The compound of the present invention is particularly suitable to be applied to, for example, electronic materials or semiconductors. When it is polymerized and thereby the π-electronic conjugation is extended, it also is expected to be applied to, for example, n-type organic semiconductors and molecular wires that are indispensable for developing molecular electronics elements.

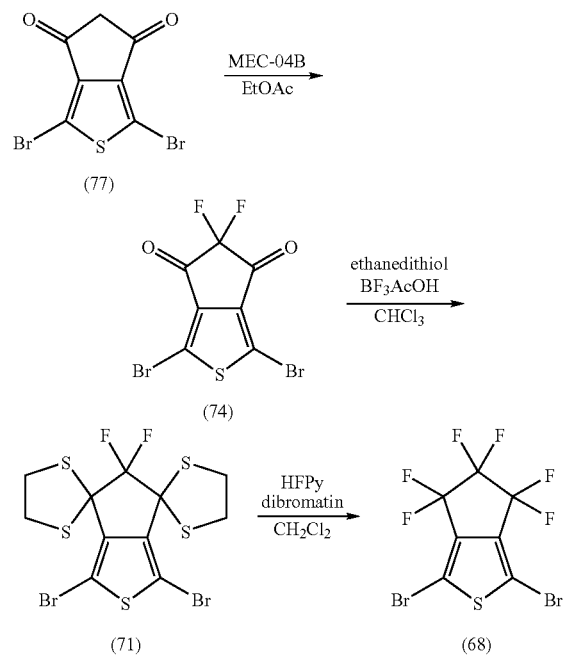

21 Claims, No Drawings

OTHER PUBLICATIONS

Scheibye, et al., "Synthesis of Thiono-, and Dithiolactones", Studies on Organophosphorus Compounds—XXVII, Tetrahedron, vol. 35, pp. 1339-1343, 1979.

Umemoto, et al., "Highly Selective Fluorinating Agents: A Counteranion-Bound N-Fluoropyridinium Salt System", J. Org. Chem. 1995, 60, 6563-6570.

Kose, et al., "Diastereoselective Photochromism of Bisbenzothienylethenes with an Oxycarbonyl-Related Functional Group on the Side Chain", J. Org. Chem. 2004, 69, 8403-8406.

Karpov, et al., "Reactions of polyfluoroindans with aluminum chloride and some other Lewis acids. Synthesis of 1,1-dichloropolyfluoroindans", Zhurnal Organicheskoi Khimii, Maik Nauka, Moscow, RU, vol. 19, No. 10, Jan. 1983, pp. 2164-2173.

Platonov, et al., "Thermolytic reactions of polyfluorinated organic compounds. XXVIII. Preparation and some properties of polyfluoroindans", Zhurnal Organicheskoi Khimii, Maik Nauka, Moscow, RU, vol. 21, No. 2, Jan. 1985, pp. 383-391.

Karpov, et al., "Fluoroindenes. Part 9. Bromine-containing polyfluoroindenes and their reaction with oleum", Izvestia Akademii Nauk SSSR. Seria Himiceskaa, Moscouw, RU., vol. 9, No. 1, Jan. 1986, pp. 2068-2074.

Platonov, et al., "Polyfluorinated arylnitrosamines", Journal of Fluorine Chemistry, vol. 114, No. 1, Mar. 2002, pp. 55-61.

Platonov, et al., "Polyfluorinated arylnitramines", Journal of Fluorine Chemistry, vol. 109, No. 2, Jul. 2001, pp. 131-139.

Platonov, et al., Interaction of N, N-dimethylperfluoroarylamines with nitric and nitrous acids, Journal of Fluorine Chemistry, vol. 116, No. 1, Jul. 2002, pp. 3-8.

Sun, et al., "Efficient synthesis and photochromic properties of 2,3-position hybrid diarylethene derivatives", Tetrahedron, Elsevier Science Publishers, vol. 59, No. 38, Sep. 2003, pp. 7615-7621.

Stavber, et al., "Selective and efficient fluorination of organic compounds in water using selectflour F-TETDA-BF4", Organic Letters, vol. 6, No. 26, Jan. 2004, pp. 4973-4976.

Zonov, et al., "Formation and skeletal transformations of perfluoroindan-1-one and perfluoroindan-1, 3-dione in the reaction of perfluoroindan with Si02/SbF5", Journal of Fluorine Chemistry, vol. 126, Dec. 2004, pp. 437-443.

CONDENSATION COMPOUND BETWEEN FLUORINATED CYCLOPENTANE RING AND AROMATIC RING, AND PROCESS FOR PRODUCING THE SAME

TECHNICAL FIELD

The present invention relates to a condensation compound of a fluorinated cyclopentane ring and an aromatic ring, and a process for producing the same.

BACKGROUND ART

Since a π-conjugated compound with a fluoroalkyl group introduced thereinto has increased electron acceptability, the compound is expected to be developed as an electron-transport material such as an n-type organic semiconductor. From this viewpoint, recently, there has been increased research into compounds with a fluoroalkyl group introduced into a thiophene ring, particularly oligothiophene (for example, Patent Documents 1 to 4). These compounds can be produced, for example, by a coupling reaction between bromothiophene and fluoroalkyl bromide or fluoroalkyl iodide in the presence of a stoichiometric amount of copper. However, the positions wherein a fluoroalkyl group can be introduced without impairing the effective conjugation of oligothiophene are limited.

On the other hand, it was proved that oligomer containing, as a base unit, thiophene having a cyclopentane ring condensed therewith had an increased effective conjugation length as compared to oligothiophene having a linear alkyl group (Non-Patent Document 1).

From the viewpoint described above, the condensed ring structure formed of a hexafluorocyclopentane ring and an aromatic ring, particularly, for example, a thiophene ring, is attracting attention. For example, a compound including a 3,3,4,4,5,5-hexafluorocyclopenta[c]thiophene structure is expected to be produced in view of, for example, improving the solubility in an organic solvent and maintaining the 7-conjugation planarity as well as lowering the LUMO level through introduction of a fluorocyclopentane ring. However, it was not possible to produce such a compound by the conventional technology.

Non-Patent Document 1: Izumi, T.; Kobashi, S.; Takimiya, K.; Aso, Y; Otsubo, T. J. Am. Chem. Soc. 2003, 125, 5286.
Patent Document 1: U.S. Patent Application Publication No. 2004/186266
Patent Document 2: U.S. Patent Application Publication No. 2004/183068
Patent Document 3: International Publication No. WO 2003/010778
Patent Document 4: European Patent Application Publication No. 1279689

DISCLOSURE OF INVENTION

Problem to be Solved by the Invention

The present invention therefore is intended to provide a condensation compound of a fluorinated cyclopentane ring and an aromatic ring, which is useful, for example, for electronic materials, and a process for producing the same.

Means for Solving Problem

In order to solve the problem described above, the compound of the present invention is a compound represented by Formula (I) below, a tautomer or stereoisomer thereof, or a salt thereof.

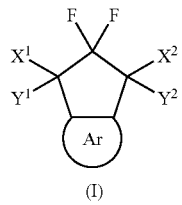

[Chemical Formula 11]

(I)

In Formula (I),

Ar is an aromatic ring and may be substituted with one or more arbitrary substituents, $X^1$ and $Y^1$ are each independently fluorine or an alkylsulfanyl group (alkylthio group), $X^1$ and $Y^1$ together form an alkylenedithio group (—S-$L^1$-S—, wherein $L^1$ is an alkylene group), or $X^1$ and $Y^1$ together with the carbon atom to which they are attached form a carbonyl group or a thiocarbonyl group, and $X^2$ and $Y^2$ are each independently fluorine or an alkylsulfanyl group (alkylthio group), $X^2$ and $Y^2$ together form an alkylenedithio group (—S-$L^2$-S—, wherein $L^2$ is an alkylene group), or $X^2$ and $Y^2$ together with the carbon atom to which they are attached form a carbonyl group or a thiocarbonyl group.

Effects of the Invention

As represented by Formula (I) above, the present invention can provide a compound including a condensed ring structure formed of a hexafluorocyclopentane ring and an aromatic ring, and a precursor thereof. Among the compounds represented by Formula (I) above, particularly a compound including a condensed ring structure formed of a hexafluorocyclopentane ring and an aromatic ring is useful, for example, for electronic materials.

DESCRIPTION OF THE INVENTION

Hereinafter, the present invention is described further in detail.

The process for producing a compound of the present invention that is represented by Formula (I) above is not particularly limited and it can be produced by any process. Preferably, however, it is produced by the production process of the present invention described below. With this production process of the present invention invented by the inventors, it became possible to produce a compound including a condensed ring structure formed of a hexafluorocyclopentane ring and an aromatic ring easily with high yield.

First, an example of the production process according to the present invention is shown in Scheme 1 below. However, Scheme 1 is a mere example and the production process according to the present invention is not limited thereto.

Scheme 1

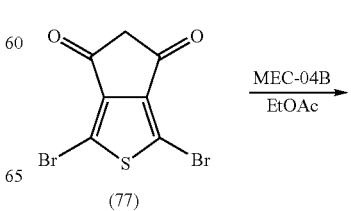

[Chemical Formula 12]

(77)

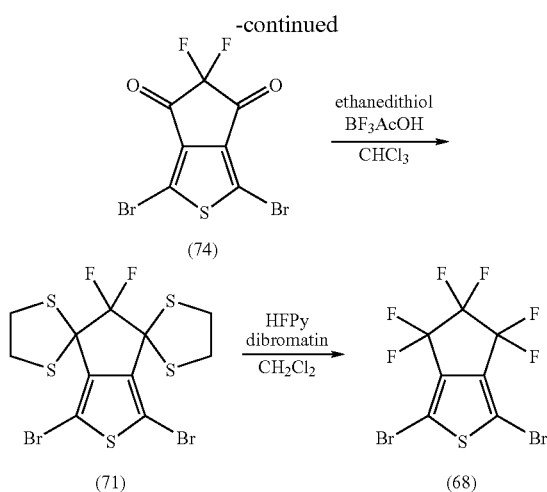

(74)

(71) → (68)

Hereinafter, the production process of the present invention is described in detail. According to the production process of the present invention, a compound represented by Formula (I) can be produced by a production process including one or at least two of three steps. The three steps include a first-stage fluorination, thioetherification or thioketonization, and a second-stage fluorination.

First, the second-stage fluorination is described. That is, the following process makes it possible to produce a compound that includes a condensed ring structure formed of a hexafluorocyclopentane ring and an aromatic ring among the compounds of the present invention represented by Formula (I), i.e. the compound in which $X^1$, $Y^1$, $X^2$, and $Y^2$ are all fluorine, a tautomer or stereoisomer thereof, or a salt thereof (hereinafter, also referred to as a "compound of the present invention containing a hexafluorocyclopentane ring").

That is, first, a precursor of the compound of the present invention containing a hexafluorocyclopentane ring that can be used herein is a compound, a tautomer or stereoisomer thereof, or a salt thereof (hereinafter also referred to as, for example, "thioether or thioketone of the present invention"), wherein in Formula (I), $X^1$ and $Y^1$ are alkylsulfanyl groups (alkylthio groups) that are identical to or different from each other, $X^1$ and $Y^1$ together form an alkylenedithio group (—S—$L^1$—S—, wherein $L^1$ is an alkylene group), or $X^1$ and $Y^1$ together with the carbon atom to which they are attached form a thiocarbonyl group, and $X^2$ and $Y^2$ are alkylsulfanyl groups (alkylthio groups) that are identical to or different from each other, $X^2$ and $Y^2$ together form an alkylenedithio group (—S—$L^2$—S—, wherein $L^2$ is an alkylene group), or $X^2$ and $Y^2$ together with the carbon atom to which they are attached form a thiocarbonyl group. In the production process of the present invention, the compound of the present invention containing a hexafluorocyclopentane ring can be produced by a production process including a step of reacting the thioether or thioketone of the present invention with a fluoride ion source in the presence of a halonium ion generator. An example of this reaction step (the second-stage fluorination) is a step of converting compound (71) into compound (68), which is shown in Scheme 1.

The reaction conditions in the reaction step are not particularly limited and can be selected suitably by referring to, for example, the conditions for a known conversion reaction from, for instance, an alkylsulfanyl group to a fluoro group (see, for example, JP 6 (1994)-135869 A). This is described below in detail.

First, the fluoride ion source is preferably hydrogen fluoride, a complex of hydrogen fluoride and amine, a complex of hydrogen fluoride and pyridine, quaternary ammonium dihydrogentrifluoride, or quaternary phosphonium dihydrogentrifluoride, and these may be used independently or two or more of them may be used in combination. An optimal fluoride ion source is, for example, a (hydrogen fluoride)$_9$/pyridine complex.

Examples of the amine include a nitrogen-containing cyclic compound such as pyridine and alkylamine such as triethylamine or diisopropylethylamine. Furthermore, the quaternary ammonium dihydrogentrifluoride and quaternary phosphonium dihydrogentrifluoride are not particularly limited, and known compounds can be used suitably. Examples of the quaternary ammonium dihydrogentrifluoride include a compound represented by Formula (V) below, and examples of the quaternary phosphonium dihydrogentrifluoride include a compound represented by Formula (VI) below.

[Chemical Formula 13]

$$R^7R^8R^9R^{10}N^+H_2F_3^-  \quad (V)$$

$$R^{11}R^{12}R^{13}R^{14}P^+H_2F_3^-  \quad (VI)$$

In Formulae (V) and (VI), $R^7$ to $R^{14}$ are each independently a hydrocarbon group such as an alkyl group, an aryl group, or a benzyl group. Examples of the quaternary ammonium dihydrogentrifluoride represented by Formula (V) include tetramethylammonium dihydrogentrifluoride, tetraethylammonium dihydrogentrifluoride, tetrabutylammonium dihydrogentrifluoride (TBAH2F3), benzyltrimethylammonium dihydrogentrifluoride, benzyltriethylammonium dihydrogentrifluoride, and cetyltrimethylammonium dihydrogentrifluoride. These can be synthesized easily from, for example, 50% fluorinated acid, potassium fluoride, and quaternary ammonium fluoride (see, for example, Bull. Soc. Chim. Fr., 910 (1986)). Examples of the quaternary phosphonium dihydrogentrifluoride represented by general formula (VI) include tetramethylphosphonium dihydrogentrifluoride, tetraethylphosphonium dihydrogentrifluoride, tetrabutylphosphonium dihydrogentrifluoride, benzyltrimethylphosphonium dihydrogentrifluoride, benzyltriethylphosphonium dihydrogentrifluoride, and cetyltrimethylphosphonium dihydrogentrifluoride.

The amount of the fluoride ion source to be used in the reaction step is not particularly limited. It is, for example, in a range of 3 equivalents to a large excess amount in terms of a fluoride ion, and preferably, for example, 3 to 5 equivalents from the viewpoints of reaction efficiency and cost.

The halonium ion generator used in the reaction step is not particularly limited and a known one can be used suitably. Examples of the halonium ion generator include 1,3-dibromo-5,5-dimethylhydantoin (DBH), N-bromosuccinimide (NBS), N-bromoacetamide (NBA), 2,4,4,6-tetrabromo-2,5-cyclohexadienone, and N-iodosuccinimide (NIS). The amount of the halonium ion generator to be used is not particularly limited. It is, for example, in a range of 3 equivalents to a large excess amount in terms of a halonium ion, and preferably, for example, 3 to 5 equivalents from the viewpoints of reaction efficiency and cost.

In the reaction step, a solvent may be used suitably if needed. The solvent is not particularly limited but is preferably one that does not hinder the intended reaction as much as possible. Examples of the solvent include aliphatic hydrocarbon such as hexane, aromatic hydrocarbon such as benzene and toluene, nitrile such as acetonitrile, ether such as diethyl ether, tetrahydrofuran, and 1,2-dimethoxyethane, and halogenated solvents such as dichloromethane, 1,2-dichloroethane, and carbon tetrachloride. These may be used independently or two or more of them may be used in combination. An optimal solvent is, for example, dichloromethane (methylene chloride).

The reaction temperature and reaction time in the reaction step are not particularly limited and can be selected suitably in consideration of, for example, the type of the substrate (the thioether or thioketone of the present invention). The reaction temperature is, for instance, in the range of −100° C. to 100° C., and is, for example, 0° C. to 80° C. from the viewpoints of reducing the reaction time and improving the reaction selectivity.

Next, the thioetherification or thioketonization, i.e. one step in the process of producing the thioether or thioketone of the present invention, is described.

The thioether or thioketone of the present invention can be produced by a production process including a step (thioetherification or thioketonization) of reacting a sulfur-containing compound with a compound of Formula (I), wherein $X^1$ and $Y^1$ together with the carbon atom to which they are attached form a carbonyl group, and $X^2$ and $Y^2$ together with the carbon atom to which they are attached form a carbonyl group, a tautomer or stereoisomer thereof, or a salt thereof (hereinafter also referred to as "diketone of the present invention"). An example of this reaction step is a step of converting compound (74) into compound (71), which is shown in Scheme 1 above.

The reaction conditions in the step of reaction with the sulfur-containing compound are not particularly limited and can be selected suitably by referring to, for example, known conditions for the reaction between ketone and a sulfur-containing compound. This is described below in detail.

Preferably, the step of reaction with the sulfur-containing compound is conducted in the presence of, for example, a Lewis acid. Preferably, the sulfur-containing compound is thiol, and more preferably, thiol and a Lewis acid are used in combination. The Lewis acid is not particularly limited and for example, a known Lewis acid can be used suitably. The Lewis acid is preferably boron trifluoride or a complex thereof. Examples of the Lewis acid include a boron trifluoride-ammonia complex, a boron trifluoride-amine complex, a boron trifluoride-ether complex (for example, a boron trifluoride-diethyl ether complex), a boron trifluoride-ester complex, a boron trifluoride-carboxylic acid complex (for example, a boron trifluoride-acetic acid complex), and a boron trifluoride-phosphine complex. An optimal Lewis acid is, for example, a boron trifluoride-acetic acid complex. Furthermore, the type of the thiol also is not particularly limited. For example, alkylthiol or alkylenedithiol that corresponds to the structure of the target thioether of the present invention can be used.

The sulfur-containing compound to be used also can be, for example, $H_2S$, $B_2S_3$, $PSBr_3$, $P_2S_5$, or a compound represented by Formula (VII) below.

[Chemical Formula 14]

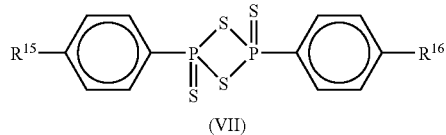

(VII)

In Formula (VII) above, $R^{15}$ and $R^{16}$ are each independently a hydrogen atom or a linear or branched alkoxy group having 1 to 6 carbon atoms. The compound in which $R^{15}$ and $R^{16}$ each are a methoxy group is known particularly as a Lawesson's reagent. The reaction caused by using the Lawesson's reagent or an analog thereof is described in, for example, M. Yokoyama et al., Synthesis, 827 (1984), M. P. Cava and M. I. Levinson, Tetrahedron, 41, 5061 (1985), M. Yoshifuji et al., Tetrahedron Lett., 35, 4379 (1994), and S, O. Lawesson et al., Tetrahedron, 35, 1339 (1979).

Next, the first-stage fluorination, i.e. one step in a process of producing the diketone of the present invention, is described.

The diketone of the present invention can be produced by a production process including a step (the first-stage fluorination) of reacting a compound represented by Formula (III) or (IV) below with a fluorinating agent. An example of this reaction step is a step of converting compound (77) into compound (74), which is shown in Scheme 1.

[Chemical Formula 15]

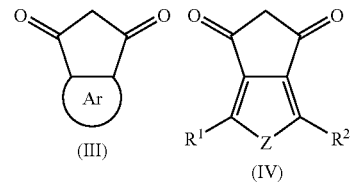

In Formula (III), Ar is identical to that of Formula (I), and in Formula (IV), Z, $R^1$, and $R^2$ are identical to those of Formula (II), respectively.

The reaction conditions in the reaction step are not particularly limited and can be selected suitably by referring to, for example, the conditions for a known fluorination reaction (see, for example, J. Org. Chem. 1995, 60, 6563 and JP 2001-354600A). This is described below in detail.

Preferably, the fluorinating agent is, for example, a fluoronium ion generator. Examples of the fluorinating agent include fluoropyridinium salts such as N-fluoropyridinium tetrafluoroborate, N-fluoropyridinium trifluoromethanesulfonate, N-fluoro-2,6-dichloropyridinium tetrafluoroborate, N-fluoro-2,6-dichloropyridinium trifluoromethanesulfonate, N-fluoro-2,4,6-trimethylpyridinium tetrafluoroborate, N-fluoro-2,4,6-trimethylpyridinium trifluoromethanesulfonate, N,N'-difluoro-2,2'-bipyridinium bis(tetrafluoroborate), N-fluoro-4,6-dimethylpyridinium-2-sulfonate, N-fluoro-4-methylpyridinium-2-sulfonate, N-fluoro-5-(trifluoromethyl)pyridinium-2-sulfonate, N-fluoro-6-(trifluoromethyl)pyridinium-2-sulfonate, N-fluoro-4,6-bis(trifluoromethyl)pyridinium-2-sulfonate, and N-fluoropyridinium pyridine heptafluorodiborate, fluorotrialkyl ammonium salts such as 1-chloromethyl-4-fluoro-1,2-diazoniabicyclo[2.2.2]octane bistetrafluoroborate, and fluoroamides such as N-fluorobenzenesulfonamide. For example, N-fluoro-6-(trifluoromethyl)pyridinium-2-sulfonate (MEC-04B) is most suitable as the fluorinating agent.

In the step of reaction with the fluorinating agent, a solvent may be used suitably. The solvent is not particularly limited. Examples of the solvent include nitrites such as acetonitrile and benzonitrile, halogen solvents such as dichloromethane, chloroform, carbon tetrachloride, 1,2-dichloroethane, and 1,1,1-trichloroethane, ethers such as diethyl ether, methyl-tert-butyl ether, and tetrahydrofuran, esters such as ethyl acetate, methyl acetate, and butyl acetate, saturated hydrocarbons such as pentane, hexane, heptane, and octane, benzenes such as benzene, toluene, xylene, and chlorobenzene, and amides such as N,N-dimethylformamide and N,N-dimethylacetamide. They may be used independently or two or more of them may be used in combination. An optimal solvent is, for example, ethyl acetate.

The reaction temperature in the step of reaction with the fluorinating agent is not particularly limited and can be selected suitably according to, for example, the type of the substrate (a compound represented by Formula (III) or (IV)). It is, for example, −20° C. to 200° C., preferably 0° C. to 100° C. If necessary, for example, trifluoromethanesulfonic acid may be added to promote the reaction.

The compound represented by Formula (III) or (IV) can be produced through known reactions used suitably in combination. For example, it may be produced by the process of Scheme 2 below or a similar process thereto, or it may be produced by a completely different process therefrom. The reactions in Scheme 2 below are described in Khanh, L. P.; Dallemagne, P.; Rault, S. Synlett, 1999, 9, 1450-1452.

Scheme 2

[Chemical Formula 16]

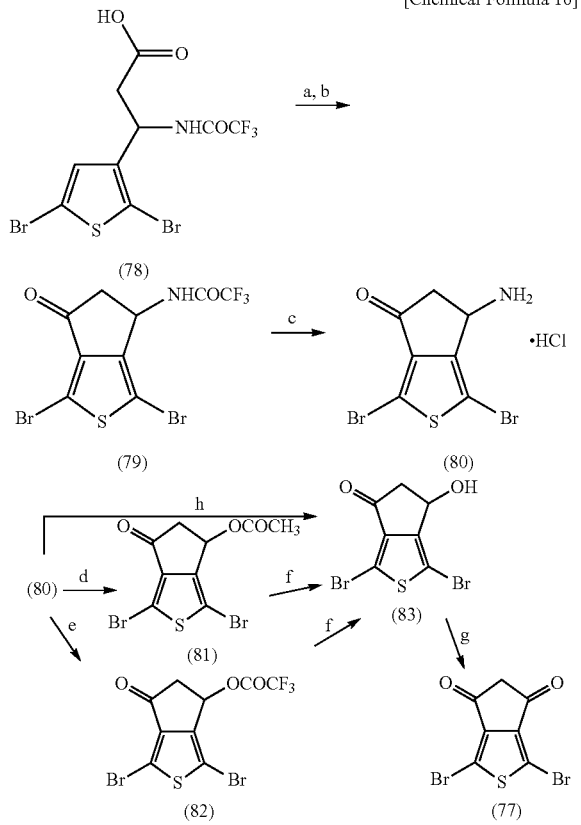

Reaction Reagents:
a: SOCl
b: AlCl$_3$, CH$_2$Cl$_2$
c: HCl, ethanol
d: NaNO$_2$, acetic acid/H$_2$O (5/10, volume/volume)
e: NaNO$_2$, trifluoroacetic acid/H$_2$O (5/10, volume/volume)
f: exposure to the air
g: CrO$_3$
h: NaNO$_2$, acetic acid/H$_2$O (2/10, volume/volume)

With respect to the process for producing the compound of the present invention containing a hexafluorocyclopentane ring from the diketone of the present invention, a process for producing it in two stages (using thioetherification or thioke-tonization and the second-stage fluorination) via the thioether or thioketone of the present invention was described. However, the compound of the present invention containing a hexafluorocyclopentane ring also can be produced in one stage by a production process including a step of reacting the diketone of the present invention with a fluorinating agent. The reaction conditions are not particularly limited and can be selected suitably by referring to, for example, the conditions for a known fluorination reaction (see, for instance JP 2001-354600 A). This is described below in detail.

Preferably, the fluorinating agent is, for instance, dialkylaminosulfur trifluoride or sulfur tetrafluoride. These may be used independently or two or more of them may be used in combination. From a point of view of safety, however, dialkylaminosulfur trifluoride is preferred. The dialkylaminosulfur trifluoride is not particularly limited. Examples thereof include diethylaminosulfur trifluoride, dimethylaminosulfur trifluoride, and bis(2-methoxyethyl)aminosulfur trifluoride.

Furthermore, the reaction may be carried out using various solvents if needed. The reaction solvent is not particularly limited. Examples of the reaction solvent include nitriles such as acetonitrile and benzonitrile, halogen solvents such as dichloromethane, chloroform, carbon tetrachloride, 1,2-dichloroethane, and 1,1,1-trichloroethane, ethers such as diethyl ether, methyl-tert-butyl ether, and tetrahydrofuran, esters such as ethyl acetate, methyl acetate, and butyl acetate, saturated hydrocarbons such as pentane, hexane, heptane, and octane, aromatic compounds such as benzene, toluene, xylene, and chlorobenzene, and amides such as N,N-dimethylformamide and N,N-dimethylacetamide. They may be used independently or two or more of them may be used in combination. Among the solvents described above, preferable ones are, for example, halogen solvents such as dichloromethane, chloroform, carbon tetrachloride, 1,2-dichloroethane, and 1,1,1-trichloroethane, as well as ethers such as diethyl ether, methyl-tert-butyl ether, and tetrahydrofuran. The reaction temperature also is not particularly limited. It is, for example, −20° C. to 200° C., preferably 0° C. to 100° C.

According to the production process of the present invention, as described above, a fluorine atom can be introduced after a cyclopentane ring structure is formed, and thereby a condensed ring structure of a hexafluorocyclopentane ring and an aromatic ring can be formed. On the contrary, conventionally, although there have been attempts to form a hexafluorocyclopentane ring by introducing a fluoroalkyl group into an aromatic ring and then cyclizing it, none of them was successful. However, the production process of the present invention made it possible to produce easily, with high yield, a compound containing a condensed ring structure formed of a hexafluorocyclopentane ring and an aromatic ring, particularly, for example, a thiophene ring, which was not possible to produce conventionally. Furthermore, in the fluorination reaction in the production process of the present invention, it also is possible to carry out fluorination using a fluorinating reagent that is inexpensive and easy to handle.

In the above, the production process of the present invention was described. With respect to, for example, the reaction conditions and reaction reagents in the production process of the present invention, those other than the examples described above also can be selected suitably. As described above, it is preferable that the compound of the present invention represented by Formula (I) be produced by the production process of the present invention. However, the production process is not limited thereto and the compound of the present invention can be produced by any process.

Next, the compound of the present invention represented by Formula (I) is described.

When there are isomers of the compound represented by Formula (I), such as a tautomer, a stereoisomer, and an optical isomer, those isomers also are embraced in the compound of the present invention. Furthermore, when the compound represented by Formula (I) and isomers thereof can form salts, the salts also are embraced in the compound of the present invention. The salts are not particularly limited and may be, for example, acid addition salts or base addition salts. Moreover, the acids that form the acid addition salts may be inorganic acids or organic acids, and the bases that form the base addition salts may be inorganic bases or organic bases. The inorganic acids are not particularly limited. Examples of the inorganic acids include sulfuric acid, phosphoric acid, hydrochloric acid, hydrobromic acid, and hydriodic acid. The organic acids also are not particularly limited. Examples of the organic acids include p-toluenesulfonic acid, methanesulfonic acid, oxalic acid, p-bromobenzenesulfonic acid, a carbonic acid, succinic acid, citric acid, benzoic acid, and acetic acid. The inorganic bases are not particularly limited. Examples of the inorganic bases include ammonium hydroxide, alkali metal hydroxide, alkaline earth metal hydroxide, carbonate, and hydrogen carbonate, more specifically, sodium hydroxide, potassium hydroxide, potassium carbonate, sodium carbonate, sodium hydrogen carbonate, potassium hydrogen carbonate, calcium hydroxide, and calcium carbonate. The organic bases also are not particularly limited. Examples of the organic bases include ethanolamine, triethylamine, and tris(hydroxymethyl)aminomethane.

The process of producing the salt of the compound of the present invention also is not particularly limited. For example, it can be produced by a process in which such an acid or a base as described above is added suitably to the compound of the present invention by a known process.

Preferably, the compound of Formula (I) is represented by Formula (II) below.

[Chemical Formula 17]

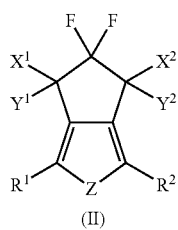

(II)

In Formula (II), $X^1$, $Y^1$, $X^2$, and $Y^2$ are identical to those used in Formula (I), respectively, and Z is an atom or an atomic group represented by any one of Formulae (i) to (ix) below.

[Chemical Formula 18]

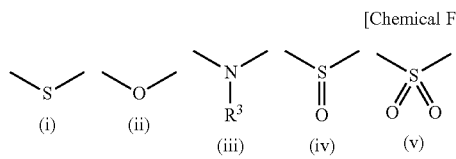

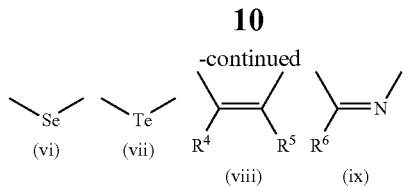

$R^1$ to $R^6$ are each independently a hydrogen atom or an arbitrary substituent, and at least two of $R^1$ to $R^6$ together with Z may form a ring.

In Formula (II), it is preferable that $R^1$ to $R^6$ be each independently a hydrogen atom, a halogen, a linear or branched, low-molecular or high-molecular chain (that may or may not contain a hetero atom in its main chain and side chain, may or may not have an unsaturated bond, and may or may not include a ring structure), a carbocyclic ring or a heterocyclic ring (that may be a monocyclic ring or a condensed ring, may be a saturated ring or an unsaturated ring, and may or may not have a substituent), an electron donating group, or an electron withdrawing group, or at least two of $R^1$ to $R^6$ together with Z may form a carbocyclic ring or a heterocyclic ring (that may be a monocyclic ring or a condensed ring, may be a saturated ring or an unsaturated ring, and may or may not have a substituent).

In Formula (II), it is preferable that $R^1$ to $R^6$ be each independently a hydrogen atom, a halogen, a linear or branched, low-molecular or high-molecular chain (that may or may not contain a hetero atom in its main chain and side chain, may or may not have an unsaturated bond, and may or may not include a ring structure), a carbocyclic ring or a heterocyclic ring that is composed of 3 to 20 atoms (that may be a monocyclic ring or a condensed ring, may be a saturated ring or an unsaturated ring, and may or may not have a substituent), a saturated or unsaturated hydrocarbon group, a hydroxy group, an alkoxy group, an alkanoyloxy group, an amino group, an oxyamino group, an alkylamino group, a dialkylamino group, an alkanoylamino group, a cyano group, a nitro group, a sulfo group, an alkyl group substituted with at least one halogen, an alkoxysulfonyl group (wherein the alkyl group thereof may be substituted with at least one halogen), an alkylsulfonyl group (wherein the alkyl group thereof may be substituted with at least one halogen), a sulfamoyl group, an alkylsulfamoyl group, a carboxyl group, a carbamoyl group, an alkylcarbamoyl group, an alkanoyl group, or an alkoxycarbonyl group, or at least two of $R^1$ to $R^6$ together with Z may form a carbocyclic ring or a heterocyclic ring (that may be a monocyclic ring or a condensed ring, may be a saturated ring or an unsaturated ring, and may or may not have a substituent).

In the present invention, the term "halogen" denotes an arbitrary halogen element and examples thereof include fluorine, chlorine, bromine, and iodine. The alkyl group is not particularly limited. Examples of the alkyl groups include a methyl group, an ethyl group, an n-propyl group, an isopropyl group, an n-butyl group, an isobutyl group, a sec-butyl group, and a tert-butyl group as well as groups containing an alkyl group in its structure (for instance, an alkoxy group, an alkylamino group, and an alkoxycarbonyl group). The unsaturated hydrocarbon group is not particularly limited. Examples of the unsaturated hydrocarbon group include a vinyl group, a 1-propenyl group, an allyl group, a propargyl group, an isopropenyl group, a 1-butenyl group, and a 2-butenyl group. The alkanoyl group is not particularly limited. Examples of the alkanoyl group include a formyl group, an acetyl group, a propionyl group, an isobutyryl group, a valeryl group, and an isovaleryl group as well as groups containing an alkanoyl group in its structure (for instance, an alkanoyloxy group and an alkanoylamino group). Furthermore, an alkanoyl group having one carbon atom should indicate a formyl group, and groups containing an alkanoyl group in its structure also are embraced therein.

In Formula (II), it is more preferable that $R^1$ to $R^6$ be each independently a hydrogen atom, a halogen, a saturated or unsaturated, linear or branched hydrocarbon chain with a substituent or no substituent, a conjugated polymer chain or an oligomer chain, a carbocyclic ring or a heterocyclic ring that is composed of 3 to 20 atoms (that may be a monocyclic ring or a condensed ring, may be a saturated ring or an unsaturated ring, and may or may not have a substituent), a hydroxy group, a linear or branched alkyl group having 1 to 18 carbon atoms, a linear or branched unsaturated hydrocarbon group having 2 to 18 carbon atoms, a linear or branched alkoxy group having 1 to 18 carbon atoms, a linear or branched alkanoyloxy group having 1 to 18 carbon atoms, an amino group, an oxyamino group, a linear or branched alkylamino group having 1 to 18 carbon atoms, a dialkylamino group (wherein an alkyl group thereof is a linear or branched alkyl group having 1 to 18 carbon atoms), a linear or branched alkanoylamino group having 1 to 18 carbon atoms, a cyano group, a nitro group, a sulfo group, a linear or branched alkyl group having 1 to 18 carbon atoms, substituted with at least one halogen, a linear or branched alkoxysulfonyl group having 1 to 18 carbon atoms (wherein the alkyl group thereof may be substituted with at least one halogen), a linear or branched alkylsulfonyl group having 1 to 18 carbon atoms (wherein the alkyl group thereof may be substituted with at least one halogen), a sulfamoyl group, a linear or branched alkylsulfamoyl group having 1 to 18 carbon atoms, a carboxyl group, a carbamoyl group, a linear or branched alkylcarbamoyl group having 1 to 18 carbon atoms, a linear or branched alkanoyl group having 1 to 18 carbon atoms, or a linear or branched alkoxycarbonyl group having 1 to 18 carbon atoms, or at least two of $R^1$ to $R^6$ together with Z may form a carbocyclic ring or a heterocyclic ring (that may be a monocyclic ring or a condensed ring, may be a saturated ring or an unsaturated ring, and may or may not have a substituent).

In Formula (II), it is further preferable that $R^1$ to $R^6$ be each independently a hydrogen atom, a halogen, a saturated or unsaturated, linear or branched hydrocarbon chain with a substituent or no substituent, a conjugated polymer chain or an oligomer chain, a carbocyclic ring or a heterocyclic ring that is composed of 3 to 20 atoms (that may be a monocyclic ring or a condensed ring, may be a saturated ring or an unsaturated ring, and may or may not have a substituent), a hydroxy group, a linear or branched alkyl group having 1 to 6 carbon atoms, a linear or branched unsaturated hydrocarbon group having 2 to 6 carbon atoms, a linear or branched alkoxy group having 1 to 6 carbon atoms, a linear or branched alkanoyloxy group having 1 to 6 carbon atoms, an amino group, an oxyamino group, a linear or branched alkylamino group having 1 to 6 carbon atoms, a dialkylamino group (wherein the alkyl group thereof is a linear or branched alkyl group having 1 to 6 carbon atoms), a linear or branched alkanoylamino group having 1 to 6 carbon atoms, a cyano group, a nitro group, a sulfo group, a linear or branched alkyl group having 1 to 6 carbon atoms, substituted with at least one halogen, a linear or branched alkoxysulfonyl group having 1 to 6 carbon atoms (wherein the alkyl group thereof may be substituted with at least one halogen), a linear or branched alkylsulfonyl group having 1 to 6 carbon atoms (wherein the alkyl group thereof may be substituted with at least one halogen), a sulfamoyl group, a linear or branched alkylsulfamoyl group having 1 to 6 carbon atoms, a carboxyl group, a carbamoyl group, a linear or branched alkylcarbamoyl group having 1 to 6 carbon atoms, a linear or branched alkanoyl group having 1 to 6 carbon atoms, or a linear or branched alkoxycarbonyl group having 1 to 6 carbon atoms, or at least two of $R^1$ to $R^6$ together with Z may form a carbocyclic ring or a heterocyclic ring (that may be a monocyclic ring or a condensed ring, may be a saturated ring or an unsaturated ring, and may or may not have a substituent).

In Formula (II), it is particularly preferable that $R^1$ to $R^6$ be each independently a hydrogen atom, a halogen, a linear hydrocarbon group with 1 to 3000 carbon atoms (each bond contained in the main chain may be a saturated bond or an unsaturated bond, and the hydrogen atom on the main chain may be substituted arbitrarily by a halogen or a methyl group), a conjugated polymer chain or an oligomer chain, a cyclic substituent having a structure formed by removing one arbitrary hydrogen atom from any one of compounds of Formulae (1) to (67) below (the cyclic substituent further may be substituted with one or more substituents, and those substituents are each independently a halogen, a methyl group, a hydroxy group, a methoxy group, an oxo group, or an amino group),

[Chemical Formula 19]

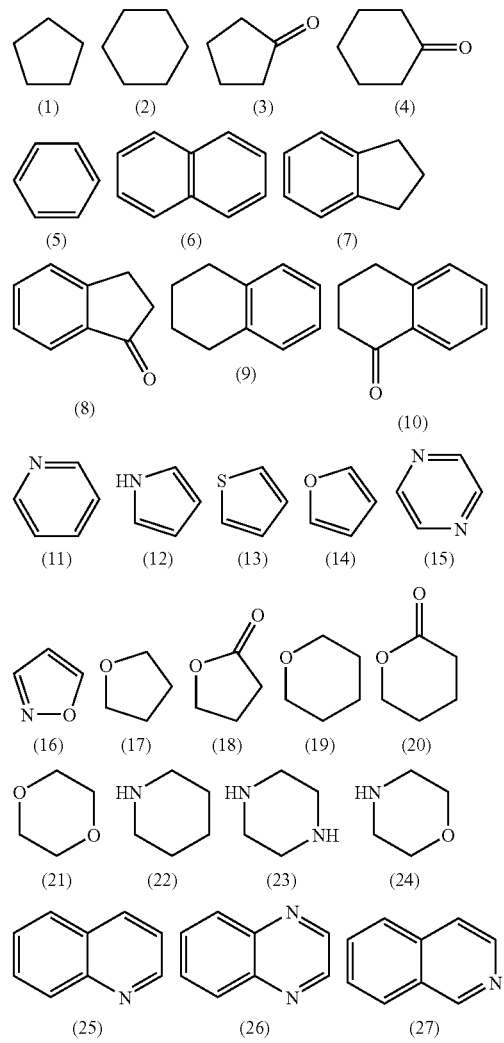

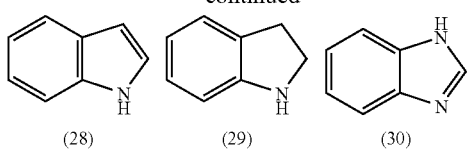
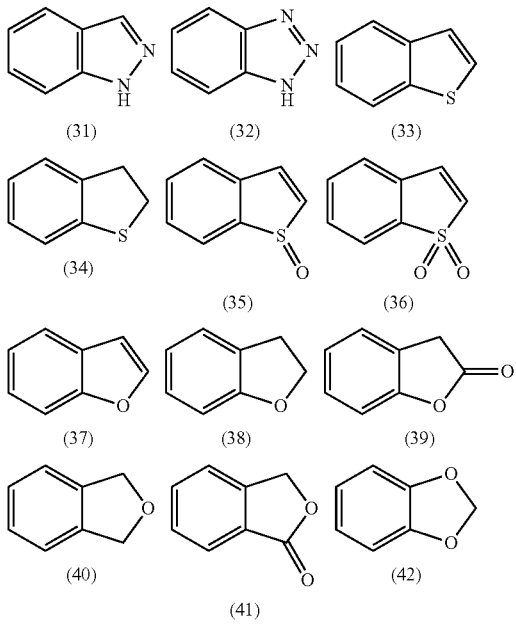
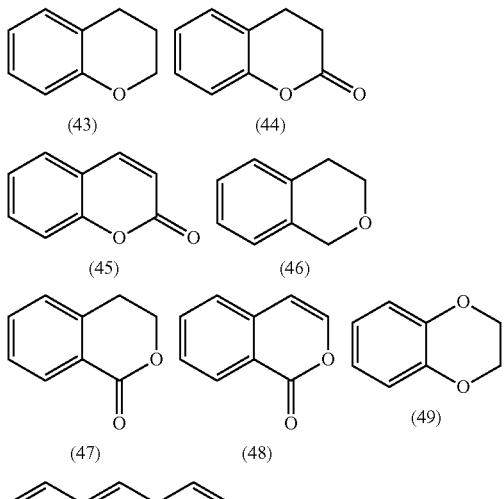
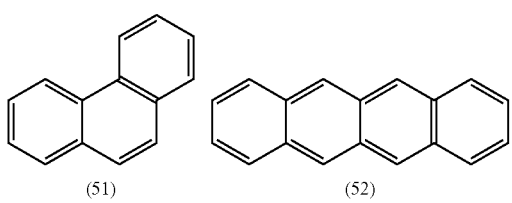
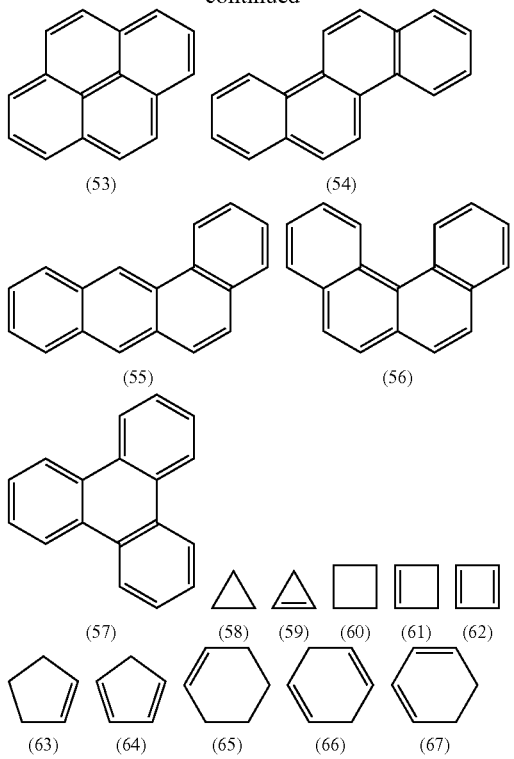

a hydroxy group, a linear or branched alkyl group having 1 to 6 carbon atoms, a linear or branched unsaturated hydrocarbon group having 2 to 6 carbon atoms, a linear or branched alkoxy group having 1 to 6 carbon atoms, a linear or branched alkanoyloxy group having 1 to 6 carbon atoms, an amino group, an oxyamino group, a linear or branched alkylamino group having 1 to 6 carbon atoms, a dialkylamino group (wherein the alkyl group thereof is a linear or branched alkyl group having 1 to 6 carbon atoms), a linear or branched alkanoylamino group having 1 to 6 carbon atoms, a cyano group, a nitro group, a sulfo group, a linear or branched alkyl group having 1 to 6 carbon atoms, substituted with at least one halogen, a linear or branched alkoxysulfonyl group having 1 to 6 carbon atoms (wherein the alkyl group thereof may be substituted with at least one halogen), a linear or branched alkylsulfonyl group having 1 to 6 carbon atoms (wherein the alkyl group thereof may be substituted with at least one halogen), a sulfamoyl group, a linear or branched alkylsulfamoyl group having 1 to 6 carbon atoms, a carboxyl group, a carbamoyl group, a linear or branched alkylcarbamoyl group having 1 to 6 carbon atoms, a linear or branched alkanoyl group having 1 to 6 carbon atoms, or a linear or branched alkoxycarbonyl group having 1 to 6 carbon atoms, or at least two of $R^1$ to $R^6$ together with Z may form a carbocyclic ring or a heterocyclic ring (that may be a monocyclic ring or a condensed ring, may be a saturated ring or an unsaturated ring, and may or may not have a substituent).

Preferably, the conjugated polymer chain or the oligomer chain is at least one selected from the group consisting of polyphenylene, oligophenylene, polyphenylenevinylene, oligophenylenevinylene, polyene, oligovinylene, polyacetylene, oligoacetylene, polypyrrole, oligopyrrole, polythiophene, oligothiophene, polyaniline, and oligoaniline (wherein these may or may not be substituted with at least one substituent). More preferably, the substituent is at least one selected from the group consisting of a halogen, a methyl group, a hydroxy group, a methoxy group, an oxo group, and an amino group. Furthermore, it is preferable that the conjugated polymer chain or the oligomer chain have a formula weight in the range of 30 to 30000.

In Formula (II), when at least two of $R^1$ to $R^6$ together with Z form a ring, it is preferable that the ring be, for example, a carbocyclic ring or a heterocyclic ring that is composed of 3 to 20 atoms (that may be a monocyclic ring or a condensed ring, may be a saturated ring or an unsaturated ring, and may or may not have a substituent), and the substituent be at least one selected from the group consisting of a halogen, a methyl group, a hydroxy group, a methoxy group, an oxo group, and an amino group.

In Formula (II), it is preferable that Z be represented by any one of Formulae (i) to (iii). A thiophene ring, a furan ring, and a pyrrole ring, particularly a thiophene ring, exhibit characteristic electric properties, and with, for example, a condensed hexafluorocyclopentane ring, it is expected to express new electric properties that were not obtained conventionally.

The compound of the present invention containing a hexafluorocyclopentane ring, i.e. a compound in which in Formula (I) or (II), $X^1$, $Y^1$, $X^2$, and $Y^2$ are all fluorine, is particularly suitable for applications to, for example, production of electronic materials or semiconductors. Especially, a compound containing, for example, a thiophene structure is expected to contribute to improving the performance of electronic materials such as semiconductors and reducing the production cost in view of, for example, improving the solubility in an organic solvent and maintaining the π-conjugation planarity as well as lowering the LUMO level through introduction of a fluorocyclopentane ring. The electronic material or semiconductor of the present invention contains the compound of the present invention containing a hexafluorocyclopentane ring and therefore has high performance.

In the compound of the present invention containing a hexafluorocyclopentane ring, it is more preferable that, for example, Z be a sulfur atom (Formula (i)), and $R^1$ and $R^2$ be each independently a hydrogen atom, chlorine, bromine, iodine, a hydroxy group, a linear or branched alkyl group having 1 to 6 carbon atoms, or a linear or branched unsaturated hydrocarbon group having 2 to 6 carbon atoms. As described above, a thiophene ring exhibits characteristic electric properties and with, for example, the condensed hexafluorocyclopentane ring, it is expected to express new electric properties that were not obtained conventionally. Among such compounds, a compound represented by, for example, any one of Formulae (68) to (70), a tautomer or stereoisomer thereof, or a salt thereof is particularly preferred.

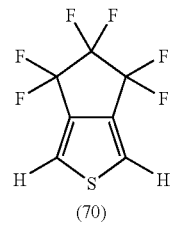

(70)

The thioether or thioketone of the present invention, i.e. a compound in which in Formula (I) or (II), $X^1$ and $Y^1$ are alkylsulfanyl groups (alkylthio groups) that are identical to or different from each other, $X^1$ and $Y^1$ together form an alkylenedithio group (—S-$L^1$-S—, wherein $L^1$ is an alkylene group), or $X^1$ and $Y^1$ together with the carbon atom to which they are attached form a thiocarbonyl group, and $X^2$ and $Y^2$ are alkylsulfanyl groups (alkylthio groups) that are identical to or different from each other, $X^2$ and $Y^2$ together form an alkylenedithio group (—S-$L^2$-S—, wherein $L^2$ is an alkylene group), or $X^2$ and $Y^2$ together with the carbon atom to which they are attached form a thiocarbonyl group, is suitable as a precursor of the compound of the present invention containing a hexafluorocyclopentane ring as described above.

In the thioether or thioketone of the present invention, it is preferable that, for example, the alkylsulfanyl groups (alkylthio groups) be linear or branched alkylsulfanyl groups (alkylthio groups) having 1 to 6 carbon atoms, and $L^1$ and $L^2$ be each independently a linear or branched alkylene group having 2 to 12 carbon atoms, and it is more preferable that $X^1$ and $Y^1$ together form an ethylenedithio group (—SCH$_2$CH$_2$S—), and $X^2$ and $Y^2$ together form an ethylenedithio group (—SCH$_2$CH$_2$S—). Furthermore, it is preferable that, for example, in Formula (I) or (II), Z be a sulfur atom (Formula (I)), and $R^1$ and $R^2$ be each independently a hydrogen atom, chlorine, bromine, iodine, a hydroxy group, a linear or branched alkyl group having 1 to 6 carbon atoms, or a linear or branched unsaturated hydrocarbon group having 2 to 6 carbon atoms. In the thioether or thioketone of the present invention, a compound according to claim 1 represented by, for example, any one of Formulae (71) to (73) below, a tautomer or stereoisomer thereof, or a salt thereof is particularly preferred.

[Chemical Formula 22]

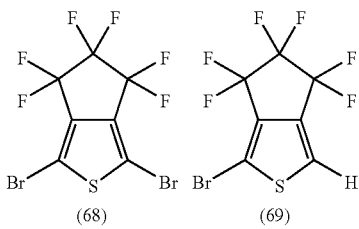

[Chemical Formula 23]

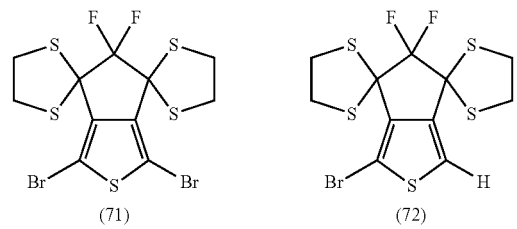

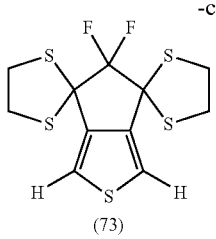

(73)

The diketone of the present invention, i.e. a compound in which in Formula (I) or (II), X¹ and Y¹ together with the carbon atom to which they are attached form a carbonyl group, and X² and Y² together with the carbon atom to which they are attached form a carbonyl group, is suitable as a precursor of the compound of the present invention containing the thioether or thioketone of the present invention or the hexafluorocyclopentane ring as described above. In the diketone of the present invention, it is preferable that in Formula (I) or (II), Z be a sulfur atom (Formula (i)), and R¹ and R² be each independently a hydrogen atom, chlorine, bromine, iodine, a hydroxy group, a linear or branched alkyl group having 1 to 6 carbon atoms, or a linear or branched unsaturated hydrocarbon group having 2 to 6 carbon atoms. Among the diketones of the present invention, a compound represented by, for example, any one of Formulae (74) to (76) below, a tautomer or stereoisomer thereof, or a salt thereof is particularly preferred.

[Chemical Formula 24]

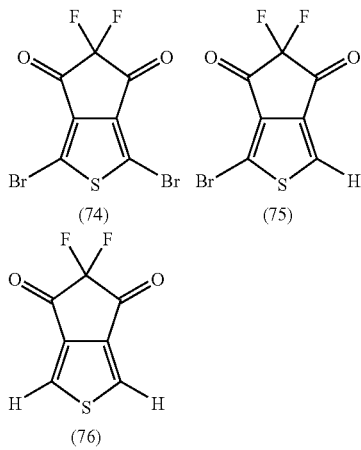

(74)  (75)

(76)

The diketone, thioether, or thioketone of the present invention can be used not only as a precursor of the compound of the present invention containing a hexafluorocyclopentane ring but also itself for production of electronic materials or semiconductors. The electronic material or semiconductor of the present invention contains the diketone, thioether, or thioketone of the present invention and therefore has high performance.

Applications of the compounds of the present invention are not limited to electronic materials or semiconductors, and they are applicable to all kinds of uses. Moreover, when the compounds of the present invention are polymerized into an oligomer or a polymer to form, for example, an oligothiophene structure, it is expected to obtain new oligomers or polymers with electron accepting-properties. Such oligomers or polymers also can be expected to be applicable to, for example, n-type organic semiconductors or molecular wires that are indispensable for developing molecular electronic elements.

EXAMPLE

Next, examples of the present invention are described.

In this example, according to Scheme 1, with compound (77) used as a starting material, compounds of the present invention represented as compounds (74), (71), and (68) were produced through, for example, a two-stage fluorination reaction. That is, first, compound (77) was fluorinated using MEC-04B and thereby compound (74) was produced. Subsequently, compound (74) was dithioacetalized and thereby compound (71) was obtained. Furthermore, in the presence of dibromatin(1,3-dibromo-5,5-dimethylhydantoin), it was desulfurized and fluorinated using HF•Py, and thereby a dibromo derivative (68) of hexafluorocyclopenta[c]thiophene was obtained. Moreover, compounds of the present invention represented as compounds (69) and (70) also were produced from the compound (68) obtained above. Scheme 1 is indicated below once again.

Scheme 1

[Chemical Formula 25]

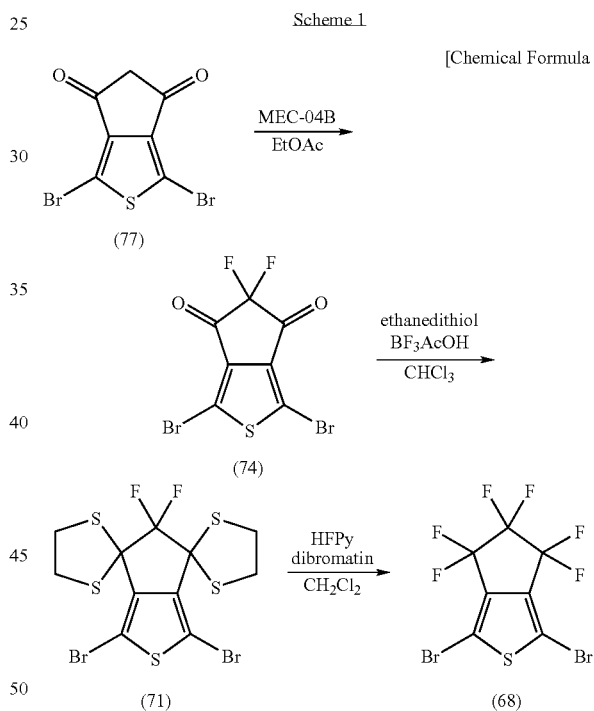

<Measurement and Other Conditions>

The nuclear magnetic resonance (NMR) spectrum was measured with JMN-270™ (270 MHz for ¹H measurement) manufactured by JEOL (JEOL Ltd.) or JMN LA-600™ (600 MHz for ¹⁹F measurement) manufactured by the same. The chemical shift is expressed in parts per million (ppm). Tetramethylsilane (TMS) was used for the internal standard, 0 ppm. The binding constant (J) is expressed in hertz. The abbreviations s, d, t, q, m, and br denote a singlet, a doublet, a triplet, a quartet, a multiplet, and a broad, respectively. In mass spectrometry (MS), measurement was carried out by the electron ionization (EI) method and the direct sample introduction (DI) method using GCMS-QP 5050A (trade name) manufactured by Shimadzu Corporation. The silica gel used for column chromatography separation was Silica gel 60N (40 to 50 μm) manufactured by Kanto Chemical Co., Inc. All chemical substances were of reagent grade and were purchased from Wako Pure Chemical Industries, Ltd., Tokyo Chemical Industry Co., Ltd., Kanto Chemical Co., Inc. Nakarai Tesque, Inc., Sigma-Aldrich Japan, K.K., or Daikin Chemicals Sales Co., Ltd. 1,3-Dibromo-4H-cyclopenta[c]thiophene-4,6(5H)-dione (77), which was the starting material of Scheme 1, was produced according to Scheme 2 with reference to the description in Khanh, L. P.; Dallemagne, P.; Rault, S. Synlett, 1999, 9, 1450-1452.

<Production of Compound>

Hereinafter, production (synthesis) of the compounds according to the present invention represented by Formulae (74), (71), (68), (69), and (70) is described in detail.

[Synthesis of 1,3-dibromo-5,5-difluoro-4H-cyclopenta[c]thiophene-4,6(5H)-dione (74)]

First, an ethyl acetate solution (5 mL) of 1,3-dibromo-4H-cyclopenta[c]thiophene-4,6(5H)-dione (1.00 g, 3.25 mmol) and N-fluoro-6-(trifluoromethyl)pyridinium-2-sulfonate (MEC-04B) (1.75 g, 7.14 mmol) was prepared. Next, this solution was stirred at 85° C. for four hours. The reaction liquid thus obtained was cooled to room temperature and was put into water, which then was subjected to extraction with ethyl acetate. The organic layer thus extracted was washed with saturated saline, which then was dried over anhydrous sodium sulfate. After an insoluble matter was filtered to be removed, the solvent was evaporated to dryness under reduced pressure. The residue thus obtained was isolated and purified by silica gel column chromatography (hexane/chloroform (1:1)). Thus target 1,3-dibromo-5,5-difluoro-4H-cyclopenta[c]thiophene-4,6(5H)-dione (74) was obtained as a light yellow solid (with a yield amount of 1.53 g and a yield of 75%). Below, the instrumental analysis data of this compound is shown.

1,3-dibromo-5,5-difluoro-4H-cyclopenta[c]thiophene-4,6(5H)-dione (74): $^{19}$F NMR (CDCl$_3$-CFCl$_3$): δ-50.67 (s). MS (m/z) 346 (M+)

[Synthesis of Compound (71)]

First, a chloroform solution (10 mL) of 1,3-dibromo-5,5-difluoro-4H-cyclopenta[c]thiophene-4,6(5H)-dione (74) (1.53 g, 4.42 mmol), 1,2-ethanedithiol (1.25 g, 13.27 mmol), and a boron trifluoride-acetic acid complex (2.50 g, 13.27 mmol) was prepared. Next, this solution was stirred at 60° C. for four hours. The reaction liquid thus obtained was cooled to room temperature and was put into water, which then was subjected to extraction with chloroform. The organic layer thus extracted was washed with saturated saline, which then was dried over anhydrous sodium sulfate. After an insoluble matter was filtered to be removed, the solvent was evaporated to dryness under reduced pressure. The residue thus obtained was isolated and purified with a silica gel column (hexane/chloroform (1:1)). Thus target compound (71) was obtained as a light purple solid (with a yield amount of 1.80 g and a yield of 82%). Below, the instrumental analysis data of this compound is shown.

Compound (71): $^1$H NMR (CDCl$_3$-TMS): δ 3.43-3.63 (m). MS (m/z) 498 (M$^+$)

[Synthesis of 1,6-dibromo-3,3,4,4,5,5-hexafluorocyclopenta[c]thiophene (68)]

First, a methylene chloride solution (10 mL) of 1,3-dibromo-5,5-dimethylhydantoin (10.32 g, 36.10 mmol) was prepared and this was cooled to −78° C. Subsequently, while the temperature of the solution was maintained at −78° C., (hydrogen fluoride)$_9$/pyridine (18 mL) was dropped thereinto, which then was stirred for ten minutes. Furthermore, while the temperature of the solution was maintained at −78° C., a methylene chloride solution (30 mL) of the compound (71) (1.80 g, 3.61 mmol) was dropped thereinto, which then was stirred for three hours. Subsequently, after the temperature of the reaction system was increased to room temperature, it further was stirred overnight. The reaction liquid thus obtained was filtered with basic alumina, and the filtrate (organic layer) was washed with an aqueous sodium hydrogen carbonate solution and then with saturated saline. Furthermore, the filtrate (organic layer) was dried over anhydrous sodium sulfate and then was filtrated, so that an insoluble matter was removed. Thereafter, the solvent was evaporated to dryness under reduced pressure. The residue thus obtained was isolated and purified with a silica gel column (hexane). Thus 1,6-dibromo-3,3,4,4,5,5-hexafluorocyclopenta[c]thiophene (68) was obtained as a colorless liquid (with a yield amount of 1.80 g and a yield of 82%). Below, the instrumental analysis data of this compound is shown.

1,6-dibromo-3,3,4,4,5,5-hexafluorocyclopenta[c]thiophene (68): $^{19}$F NMR (CDCl$_3$-CFCl$_3$): δ−110.71 (m) and −126.08 (m). MS (m/z) 390 (M$^+$)

[Synthesis of 1-bromo-3,3,4,4,5,5-hexafluorocyclopenta[c]thiophene (69) and 3,3,4,4,5,5-hexafluorocyclopenta[c]thiophene (70)]

First, a tetrahydrofuran solution (2 mL) of 1,3-dibromo-3,3,4,4,5,5-hexafluorocyclopenta[c]thiophene (68) (100 mg, 0.257 mmol) and tetramethylethylene diamine (47 mg, 0.405 mmol) was prepared. Next, this solution was cooled to −78° C. Subsequently, while the temperature thereof was maintained, n-butyllithium (0.17 mL, 0.270 mmol) was dropped thereinto, which then was stirred for one hour. Thereafter, 1 mL of water was added thereto to stop the reaction, which then was subjected to extraction with hexane. The organic layer thus extracted was washed with saturated saline, was dried over anhydrous sodium sulfate, and then was filtrated, so that an insoluble matter was removed. Thereafter, the solvent was evaporated to dryness under reduced pressure. The residue thus obtained was isolated and purified by silica gel column chromatography (developing solvent: hexane). Thus 1-bromo-3,3,4,4,5,5-hexafluorocyclopenta[c]thiophene (69) was obtained as a colorless liquid (with a yield amount of 50 mg and a yield of 64%). Below, the instrumental analysis data of this compound (69) is shown.

1-bromo-3,3,4,4,5,5-hexafluorocyclopenta[c]thiophene (69): $^1$HNMR (CDCl$_3$-TMS): δ 7.75 (s), MS (m/z) 312 (M$^+$)

In the reaction described above, 3,3,4,4,5,5-hexafluorocyclopenta[c]thiophene (70) also was isolated by silica gel column chromatography (developing solvent: hexane) and thereby the generation thereof was checked by the instrumental analysis.

In this example, the compounds of the present invention produced as described above were measured for their electric properties. As a result, all of the compounds exhibited characteristic properties suitable for application to electronic materials or semiconductors, particularly n-type organic semiconductors.

INDUSTRIAL APPLICABILITY

As described above, the present invention can provide a condensation compound formed of a fluorinated cyclopentane ring and an aromatic ring, which is useful, for example, for electronic materials, and a process for producing the same. The compounds of the present invention that contain a hexafluorocyclopentane ring are particularly suitable for application to, for example, electronic materials or semiconductors. Especially, the compounds containing, for instance, a thiophene structure exhibit characteristic electric properties and with, for example, a condensed hexafluorocyclopentane ring, they also are expected to express new electric properties that were not obtained conventionally. Furthermore, the application of the compounds according to the present invention is not limited to electronic materials or semiconductors and they are applicable to all kinds of uses. Moreover, when the compounds of the present invention are polymerized into an oligomer or a polymer to form, for example, an oligothiophene structure, the π-electronic conjugation is extended and thereby it is expected to obtain new oligomers or polymers with electron accepting-properties. Such oligomers or polymers also can be expected to be applicable to, for example, n-type organic semiconductors or molecular wires that are indispensable for developing molecular electronics elements.

The invention claimed is:

1. A compound represented by Formula (II) below, a tautomer or stereoisomer thereof, or a salt thereof,

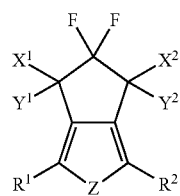

wherein all of $X^1$, $Y^1$, $X^2$, and $Y^2$ are a fluorine atom; or
$X^1$ and $Y^1$ together form an alkylenedithio group (—S-$L^1$-S—, wherein $L^1$ is an alkylene group), or
$X^1$ and $Y^1$ together with a carbon atom to which $X^1$ and $Y^1$ are attached form a carbonyl group or a thiocarbonyl group, and
$X^2$ and $Y^2$ are each independently, a fluorine atom or an alkylsulfanyl group (alkylthio group), or
$X^2$ and $Y^2$ together form a alkylenedithio group (—S-$L^2$-S—, wherein $L^2$ is an alkylene group), or
$X^2$ and $Y^2$ together with a carbon atom to which $X^2$ and $Y^2$ are attached form a carbonyl group or a thiocarbonyl group; or
$X^1$ and $Y^1$ are each independently, a fluorine atom or an alkylsulfanyl group (alkylthio group), or
$X^1$ and $Y^1$ together form an alkylenedithio group (—S-$L^1$-S—, wherein $L^1$ is an alkylene group), or
$X^1$ and $Y^1$ together with a carbon atom to which $X^1$ and $Y^1$ are attached form a carbonyl group or a thiocarbonyl group, and
$X^2$ and $Y^2$ together form a alkylenedithio group (—S-$L^2$-S—, wherein $L^2$ is an alkylene group), or
$X^2$ and $Y^2$ together with a carbon atom to which $X^2$ and $Y^2$ are attached form a carbonyl group or a thiocarbonyl group; and
Z is an atom or an atomic group represented by any one of Formulae (i) to (vii),

 (i)

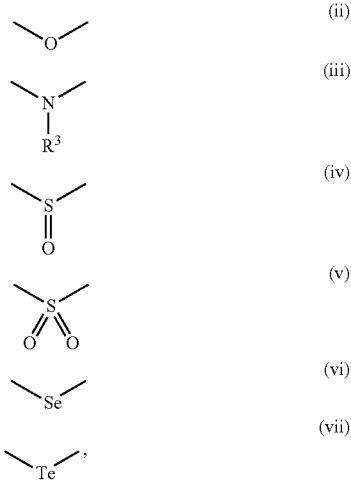

wherein $R^1$ to $R^3$ are each independently, a hydrogen atom or a substituent.

2. The compound according to claim 1, the tautomer or stereoisomer thereof, or the salt thereof, wherein $R^1$ to $R^3$ are each independently a hydrogen atom, a halogen, a linear or branched, low-molecular or high-molecular chain (that may or may not contain a hetero atom in its main chain and side chain, may or may not have an unsaturated bond, and may or may not include a ring structure), a carbocyclic ring or a heterocyclic ring that is composed of 3 to 20 atoms (that may be a monocyclic ring or a condensed ring, may be a saturated ring or an unsaturated ring, and may or may not have a substituent), a saturated or unsaturated hydrocarbon group, a hydroxy group, an alkoxy group, an alkanoyloxy group, an amino group, an oxyamino group, an alkylamino group, a dialkylamino group, an alkanoylamino group, a cyano group, a nitro group, a sulfo group, an alkyl group substituted with at least one halogen, an alkoxysulfonyl group (wherein an alkyl group thereof may be substituted with at least one halogen), an alkylsulfonyl group (wherein an alkyl group thereof may be substituted with at least one halogen), a sulfamoyl group, an alkylsulfamoyl group, a carboxyl group, a carbamoyl group, an alkylcarbamoyl group, an alkanoyl group, or an alkoxycarbonyl group, or at least two of $R^1$ to $R^3$ together with Z form a carbocyclic ring or a heterocyclic ring (that may be a monocyclic ring or a condensed ring, may be a saturated ring or an unsaturated ring, and may or may not have a substituent).

3. The compound according to claim 1, the tautomer or stereoisomer thereof, or the salt thereof, wherein Z is represented by any one of Formulae (i) to (iii).

4. The compound according to claim 1, the tautomer or stereoisomer thereof, or the salt thereof,
wherein all of $X^1$, $Y^1$, $X^2$, and $Y^2$ are a fluorine atom.

5. The compound according to claim 1, the tautomer or stereoisomer thereof, or the salt thereof,
wherein Z is a sulfur atom (Formula (i)), and $R^1$ and $R^2$ are each independently, a hydrogen atom, chlorine, bromine, iodine, a hydroxy group, a linear or branched alkyl group having 1 to 6 carbon atoms, or a linear or branched unsaturated hydrocarbon group having 2 to 6 carbon atoms.

6. A compound, a tautomer or stereoisomer thereof, or a salt thereof, represented by any one of Formulae (68) to (70) below,

(68)
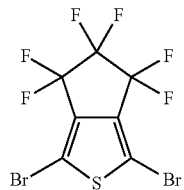

(69)
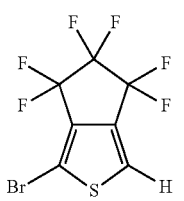

(70)
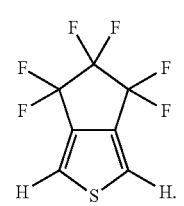

7. The compound according to claim 1, the tautomer or stereoisomer thereof, or the salt thereof, wherein $X^1$ and $Y^1$ together form the alkylenedithio group (—S-$L^1$-S—, wherein $L^1$ is an alkylene group), or $X^1$ and $Y^1$ together with the carbon atom to which $X^1$ and $Y^1$ are attached form the thiocarbonyl group, and $X^2$ and $Y^2$ together form the alkylenedithio group (—S-$L^2$-S—, wherein $L^2$ is an alkylene group), or $X^2$ and $Y^2$ together with the carbon atom to which $X^2$ and $Y^2$ are attached form the thiocarbonyl group.

8. A compound, a tautomer or stereoisomer thereof, or a salt thereof, represented by any one of Formulae (71) to (73) below,

(71)
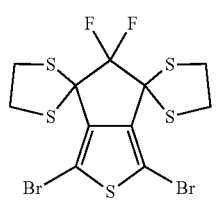

(72)
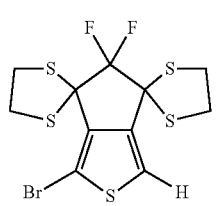

(73)
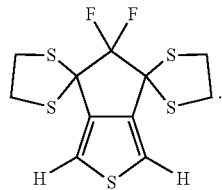

9. The compound according to claim 1, the tautomer or stereoisomer thereof, or the salt thereof, wherein $X^1$ and $Y^1$ together with the carbon atom to which $X^1$ and $Y^1$ are attached form a carbonyl group, and $X^2$ and $Y^2$ together with the carbon atom to which $X^2$ and $Y^2$ are attached form a carbonyl group.

10. A compound, a tautomer or stereoisomer thereof, or a salt thereof, represented by any one of Formulae (74) to (76) below,

(74)
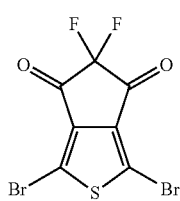

(75)
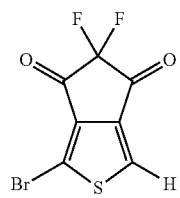

(76)
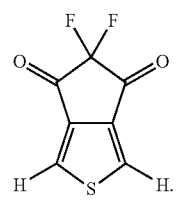

11. A process for producing a compound represented by Formula (II-1) below:

(II-1)
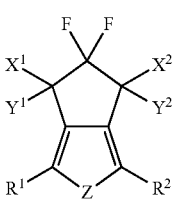

wherein all of $X^1$, $Y^1$, $X^2$ and $Y^2$ are a fluorine atom; and

Z is an atom or an atomic group represented by any one of Formulae (i) to (vii),

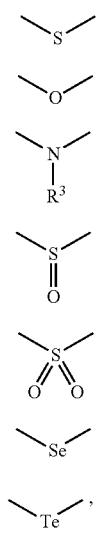

wherein $R^1$ to $R^3$ are each independently, a hydrogen atom or a substituent, comprising reacting a compound, a tautomer or stereoisomer thereof, or a salt thereof, represented by Formula (II-2) below:

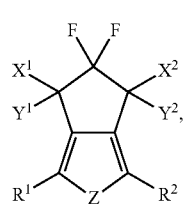

(II-2)

wherein $X^1$ and $Y^1$ together form an alkylenedithio group (—S-$L^1$-S—, wherein $L^1$ is an alkylene group), or $X^1$ and $Y^1$ together with a carbon atom to which $X^1$ and $Y^1$ are attached form a thiocarbonyl group, and $X^2$ and $Y^2$ are each independently, an alkylsulfanyl group (alkylthio group), or $X^2$ and $Y^2$ together form an alkylenedithio group (—S-$L^2$-S— wherein $L^2$ is an alkylene group), or $X^2$ and $Y^2$ together with a carbon atom to which $X^2$ and $Y^2$ are attached form a thiocarbonyl group; or $X^1$ and $Y^1$ are each independently, an alkylsulfanyl group (alkylthio group)

$X^2$ and $Y^2$ together form an alkylenedithio group (—S-$L^2$-S— wherein $L^2$ is an alkylene group), or $X^2$ and $Y^2$ together with the carbon atom to which $X^2$ and $Y^2$ are attached form a thiocarbonyl group; and Z is an atom or an atomic group represented by any one of Formulae (i) to (vii),

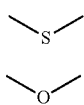

wherein $R^1$ to $R^3$ are each independently, a hydrogen atom or a substituent, with a fluoride ion source in the presence of a halonium ion generator.

12. The process according to claim 11, wherein the fluoride ion source is hydrogen fluoride, a complex of hydrogen fluoride and amine, a complex of hydrogen fluoride and pyridine, quaternary ammonium dihydrogentrifluoride, or quaternary phosphonium dihydrogentrifluoride.

13. The process according to claim 11, wherein the halonium ion generator is 1,3-dibromo-5,5-dimethylhydantoin (DBH), N-bromosuccinimide (NBS), N-bromoacetamide (NBA), 2,4,4,6-tetrabromo-2,5-cyclohexadienone, or N-iodosuccinimide (NIS).

14. A process for producing a compound, a tautomer or stereoisomer thereof, or a salt thereof, represented by Formula (II) below:

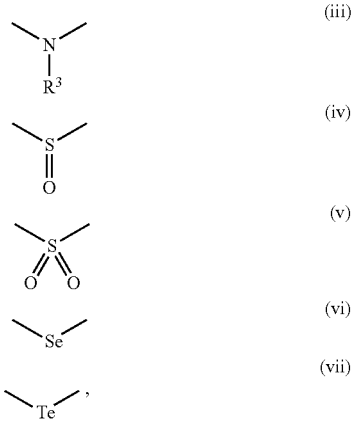

(II)

wherein $X^1$ and $Y^1$ together form an alkylenedithio group (—S-$L^1$-S—, wherein $L^1$ is an alkylene group), or $X^1$ and $Y^1$ together with a carbon atom to which $X^1$ and $Y^1$ are attached form a thiocarbonyl group, and $X^2$ and $Y^2$ together form an alkylenedithio group (—S-$L^2$-S—, wherein $L^2$ is an alkylene group), or $X^2$ and $Y^2$ together with a carbon atom to which $X^2$ and $Y^2$ are attached form a thiocarbonyl group; and Z is an atom or an atomic group represented by any one of Formulae (i) to (vii),

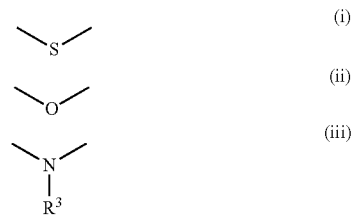

-continued

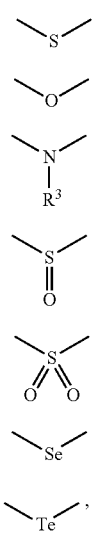

wherein $R^1$ to $R^3$ are each independently, a hydrogen atom or a substituent, comprising reacting a compound, a tautomer or stereoisomer thereof, or a salt thereof, represented by Formula (II) below:

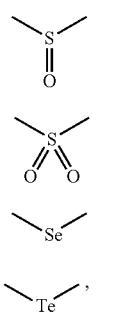

wherein $X^1$ and $Y^1$ together with the carbon atom to which $X^1$ and $Y^1$ are attached form a carbonyl group, and
$X^2$ and $Y^2$ together with the carbon atom to which $X^2$ and $Y^2$ are attached form a carbonyl group; and
Z is an atom or an atomic group represented by any one of Formulae (i) to (vii),

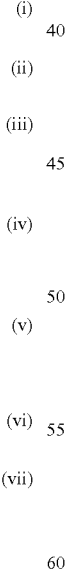

wherein $R^1$ to $R^3$ are each independently, a hydrogen atom or a substituent, with a sulfur-containing compound.

15. The process according to claim 14, wherein the sulfur-containing compound is thiol.

16. The process according to claim 14, wherein the step of reaction with the sulfur-containing compound is carried out in the presence of a Lewis acid.

17. A process for producing a compound according to claim 9, a tautomer or stereoisomer thereof, or a salt thereof, comprising reacting a compound represented by Formula (IV) below with a fluorinating agent,

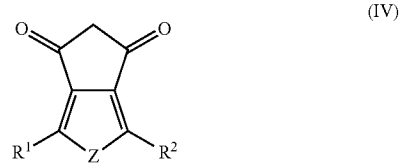

wherein in Formula (IV), Z, $R^1$, and $R^2$ are those of Formula (II) for claim 9 above, respectively.

18. The process according to claim 17, wherein the fluorinating agent is a fluoronium ion generator.

19. A process for producing a compound represented by Formula (II-3) below:

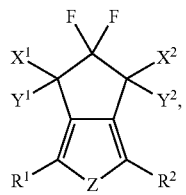

wherein all of $X^1$, $Y^1$, $X^2$, and $Y^2$ are a fluorine atom, and
Z is an atom or an atomic group represented by any one of Formulae (i) to (vii),

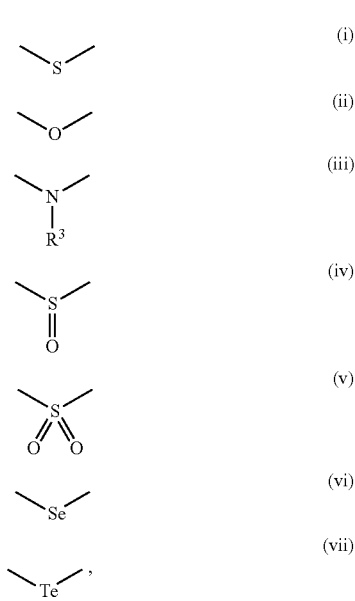

wherein $R^1$ to $R^3$ are each independently, a hydrogen atom or a substituent, comprising reacting a compound, a tautomer or stereoisomer thereof, or a salt thereof, represented by Formula (II-4) below:

(II-4)

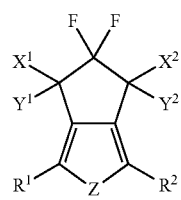

wherein $X^1$ and $Y^1$ together with a carbon atom to which $X^1$ and $Y^1$ are attached form a carbonyl group, and
$X^2$ and $Y^2$ together with a carbon atom to which $X^2$ and $Y^2$ are attached form a carbonyl group; and
Z is an atom or an atomic group represented by any one of Formulae (i) to (vii), (i)
\\S/

(ii)
\\O/

(iii)
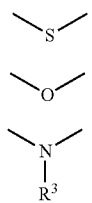

(iv)

(v)

(vi)

(vii)

wherein $R^1$ to $R^3$ are each independently, a hydrogen atom or a substituent, with a fluorinating agent.

20. An electronic material comprising a compound according to claim 1, a tautomer or stereoisomer thereof, or a salt thereof.

21. A semiconductor comprising a compound according to claim 1, a tautomer or stereoisomer thereof, or a salt thereof.

\* \* \* \* \*